United States Patent
Sahin et al.

(10) Patent No.: US 9,526,904 B2
(45) Date of Patent: Dec. 27, 2016

(54) SYSTEM AND METHOD FOR NEURAL STIMULATION VIA OPTICALLY ACTIVATED FLOATING MICRODEVICES

(71) Applicants: Mesut Sahin, Clifton, NJ (US); Selim Unlu, Boston, MA (US); David S Freedman, Boston, MA (US); Ammar R Abdo, Belleville, NJ (US)

(72) Inventors: Mesut Sahin, Clifton, NJ (US); Selim Unlu, Boston, MA (US); David S Freedman, Boston, MA (US); Ammar R Abdo, Belleville, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 0 days.

(21) Appl. No.: 13/871,654

(22) Filed: Apr. 26, 2013

(65) Prior Publication Data

US 2013/0338731 A1    Dec. 19, 2013

Related U.S. Application Data

(60) Provisional application No. 61/639,470, filed on Apr. 27, 2012.

(51) Int. Cl.
| | | |
|---|---|---|
| *A61N 1/378* | (2006.01) | |
| *A61N 1/375* | (2006.01) | |
| *A61N 1/36* | (2006.01) | |
| *A61N 1/372* | (2006.01) | |

(52) U.S. Cl.
CPC ............. *A61N 1/378* (2013.01); *A61N 1/3606* (2013.01); *A61N 1/3756* (2013.01); *A61N 1/3787* (2013.01); *A61N 1/37205* (2013.01); *A61N 1/36067* (2013.01); *A61N 1/36075* (2013.01)

(58) Field of Classification Search
CPC ............. A61N 1/3787; A61N 1/37205; A61N 1/37217; A61N 1/378; H02J 17/00
See application file for complete search history.

(56) References Cited

U.S. PATENT DOCUMENTS

| 7,177,698 B2* | 2/2007 | Klosterman ......... A61N 1/3605 607/60 |
|---|---|---|
| 2006/0085051 A1* | 4/2006 | Fritsch ............................ 607/61 |

OTHER PUBLICATIONS

Loeb, et al., Injectable Microstimulator for Functional Electrical Stimulation, Medical and Biological Engineering and Computing, vol. 29, No. 6, pp. NS13-NS19, 1991.

(Continued)

*Primary Examiner* — Michael Kahelin
(74) *Attorney, Agent, or Firm* — McCarter & English, LLP (57) ABSTRACT

Stimulation of the central nervous system can be useful for treating neurological disorders. Wireless neurostimulating devices have the benefit that they can float in tissue and do not experience the sheering caused by tethering tension that connecting wires impose on the stimulators. An optically powered, logic controlled, CMOS microdevice that can decode telemetry data from an optical packet is a way of implementing wireless, addressable, microstimulators. Through the use of an optical packet, different devices can be addressed for stimulation, allowing spatially selective activation of neural tissue. The present invention, involves such a neural stimulation device, specifically an optically powered CMOS circuit that decodes telemetry data and determines whether it has been addressed.

5 Claims, 6 Drawing Sheets

(56) References Cited

OTHER PUBLICATIONS

Cameron, et al., Micromodular Implants to Provide Electrical Stimulation of Paralyzed Muscles and Limbs, Biomedical Engineering, IEEE Transactions on, vol. 44, No. 9, pp. 781-790, 1997.

Suaning, et al., CMOS Neurostimulation ASIC with 100 Channels, Scaleable Output, and Bidirectional Radio-Frequency Telemetry, Biomedical Engineering, IEEE Transactions on, vol. 48, No. 2, pp. 248-260, 2001.

Loeb, et al., BION™ System for Distributed Neural Prosthetic Interfaces, Medical Engineering and Physics, vol. 23, No. 1, pp. 9-18, 2001.

Yaroslavsky, et al., Optical Properties of Selected Native and Coagulated Human Brain Tissues in Vitro in the Visible and Near Infrared Spectral Range, Physics in Medicine and Biology, vol. 47, p. 2059, 2002.

McCreery, et al., Arrays for Chronic Functional Microstimulation of the Lumbosacral Spinal Cord, Neural Systems and Rehabilitation Engineering, IEEE Transactions on, vol. 12, No. 2, pp. 195-207, 2004.

Bradley, et al., Visuotopic Mapping Through a Multichannel Stimulating Implant in Primate V1, Journal Neurophysiology, vol. 93, No. 3, pp. 1659-1670, 2005.

Otto, et al., Cortical Microstimulation in Auditory Cortex of Rat Elicits Best-Frequency Dependent Behaviors, Journal of Neural Engineering, vol. 2, No. 2, p. 42, 2005.

Boyden, et al., Millisecond-Timescale Genetically Targeting Optical Control of Neural Activity, Nature Neuroscience, vol. 8, No. 9, pp. 1263-1268, 2005.

Loudin, et al., Optoelectronic Retinal Prosthesis: System Design and Performance, Journal of Neural Engineering, vol. 4, No. 1, p. S72, 2007.

Han, et al., Multiple-Color Optical Activation, Silencing, and Desynchronization of Neural Activity, With Single-Spike Temporal Resolution, PLoS ONE, vol., 2, No. 3, p. e299, 2007.

Sahin, et al., Finite Element Analysis of a Floating Microstimulator, Neural Systems and Rehabilitation Engineering, IEEE Transactions on, vol. 15, No. 2, pp. 227-234, 2007.

Abdo, et al., NIR Light Penetration Depth in the Rat Peripheral Nerve and Brain Cortex, in Engineering in Medicine and Biology Society, 2007 Annual International Conference of the IEEE, 2007, pp. 1723-1725.

Huang, et al., A High-Speed and High-Responsivity Photodiode in Standard CMOS Technoology, Photonics Technology Letters, IEEE, vol. 19, No. 4, pp. 197-199, 2007.

Song, et al., A Microscale Photovoltaic Neurostimulator for Fiber Optic Delivery of Functional Electrical Stimulation, Journal of Neural Engineering, vol. 4, pp. 213-218, 2007.

Abdo, et al., In Vitro Testing of Floating Light Activated Micro-Electrical Stimulators, in Engineering in Medicine and Biology Society, 2009 Annual International Conference of the IEEE, pp. 626-629, 2009.

Abdo, et al., NIR Light Penetration in Unfrozen Samples of Rat Brain Gray Matter, in Bioengineering Conference, 2009 IEEE Annual Northeast, pp. 1-2, 2009.

\* cited by examiner

SYSTEM AND METHOD FOR NEURAL STIMULATION VIA OPTICALLY ACTIVATED FLOATING MICRODEVICES

CROSS REFERENCE TO RELATED PATENTS

This application claims priority to U.S. Provisional patent No. 61/639,470, filed Apr. 27, 2012.

STATEMENT REGARDING FEDERALLY SPONSORED RESEARCH

The research leading to the present invention was supported, in part by federal grants including the NIH Grants NIH R21-NS 050757-01A1 and NIH/NIBIB R01 EB009100-01. Accordingly, the United States Government may have certain rights in the invention.

FIELD OF THE INVENTION

This invention relates to an apparatus and method for the electrical stimulation of the central nervous system useful in the treatment of a number of disorders.

BACKGROUND OF THE INVENTION

Electrical stimulation of the central nervous system (CNS) has been used as a treatment for a number of disorders. Microelectrode arrays are used to achieve high spatial selectivity with micro-machined penetrating shanks. Caused by tethering forces from interconnects, the rigid bodies of these shanks result in chronic responses that include scarring and reduces the effectiveness of such micro stimulators.

Wireless stimulators are expected to mitigate this chronic response because they have no wires to cause forces from micromotion and therefore are free to float. Some examples of wireless stimulators include addressable radio-frequency (RF) microstimulators and an RF microstimulator array. These devices receive energy and communication information from RF electromagnetic waves. This necessitates an inductive coil that limits the minimum size of the device.

Photovoltaic stimulators have the ability to float, similar to RF stimulators, but they convert optical energy into electrical energy using semiconductors. Fiber guided high-efficiency photovoltaic stimulators have been used for neurostimulation. Retinal photovoltaic arrays exploit the two-dimensional nature of sight and utilize an image projection system to selectively activate photodiodes in an array. Additionally, gene therapy technologies have enabled photonic neurostimulation in neurons that have algal proteins.

Figure 1:
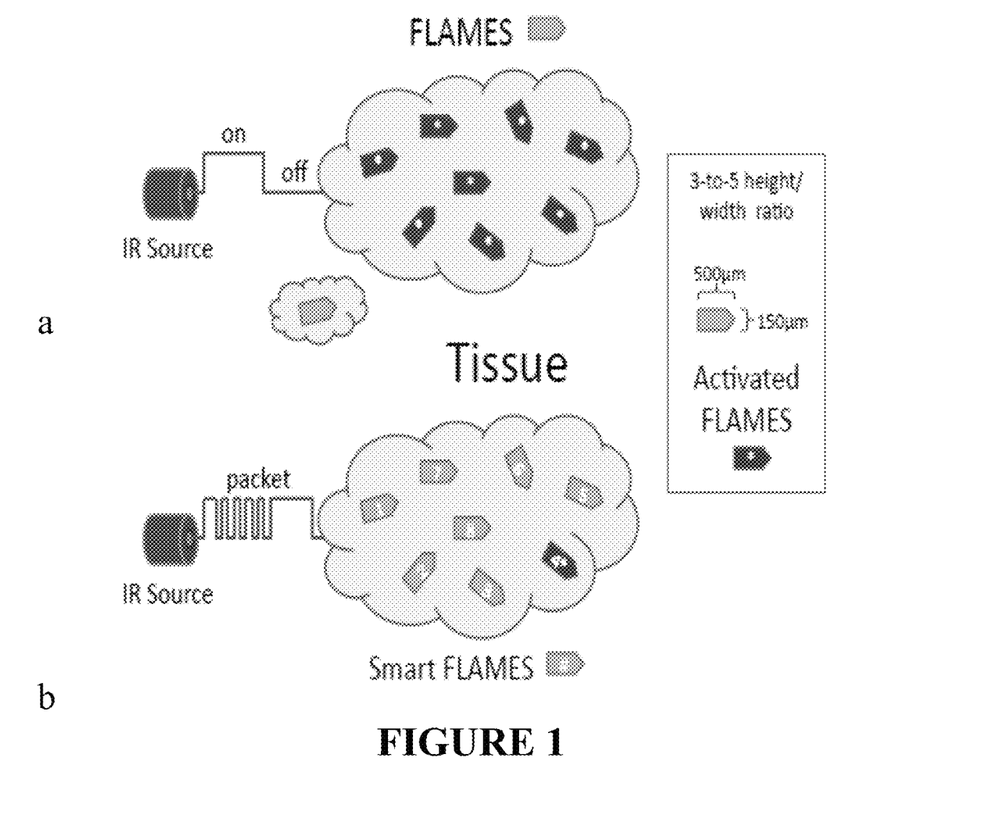
FIG. 1 illustrates indiscriminate activation of FLAMES devices as compared to the selective activation of a Smart FLAMES device showing use of an optical packet to determine the specific address to activate, which in this case, is four.

Floating Light Activated Microelectrical Stimulators (FLAMES) with have been micromachined and tested in tissue. FLAMES devices exploit the dispersive nature of white and grey matter to cause neurostimulation without a focused optical path. As seen in FIG. 1a, FLAMES devices are indiscriminately activated whenever enough optical energy is converted into electrical energy. However, there is a need to have selectively addressable stimulators to allow more directed stimulation which would open up a wide range of potential applications that are currently not possible.

SUMMARY OF THE INVENTION

The present invention relates to a selectively addressable smart floating light-activated micro device. Advantageously, the micro device is wireless and can float in tissue. The microdevice is activated through one-way communication channel that consists of an encoded optical pulse packet.

Another embodiment of the invention relates to a system comprising such selectively addressable device and a device operated in the photovoltaic region to induce stimulation.

The present invention further involves a device with a semiconductor diode junction operated in the photovoltaic region to induce stimulation. The designed electronics of the present invention demonstrate the feasibility of addressing a wireless micro-stimulator and delivering the stimulus pulse through the same device.

BRIEF DESCRIPTION OF THE DRAWINGS

So that those having ordinary skill in the art will have a better understanding of how to make and use the invention, reference is made to the accompanying figures wherein.

DETAILED DESCRIPTION OF INVENTION

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

Neurostimulation delivers a localized electrical signal to neural tissue, spinal cord, or peripheral nerves. It is useful for treating neurodegenerative diseases, such as, for example, for reducing the tremors that occur in Parkinson's patients or for treating pain resulting from chronic pain conditions. There are two types of implantable neurostimulation systems: those that are completely implantable and others that have both external and internal components. Current neurostimulation systems that are completely implantable include an implanted power source, such as a battery. These systems are not suitable for implantation into the brain due to size constraints and biocompatibility concerns. Other systems have percutaneous wires connecting the external system to the implanted part of the system for power delivery and telemetry. Percutaneous wires are problematic in the body as they can increase the likelihood of infection at the point of skin penetration. There are also other problems that can result, for example, in systems that make use of percutaneous neurostimulators that penetrate neural tissue while being anchored in the tissue outside the dura mater. Because these neurostimulators are rigid, the movement between neural tissue and the outside tissue results in mechanical damage to the neural tissue. Neurostimulation through a wireless implantable device presents a solution to these problems.

Furthermore, neurostimulators should be addressable so that specific areas in the neural tissue can be activated to allow controlled multisite stimulation. One design approach for the fabrication of addressable, light powered, wireless neurostimulators is to fabricate devices that exhibit wavelength specificity, thus allowing addressability through irradiation at various wavelengths. The main constraint of this approach is that only a few different devices can be individually addressed.

The present invention relates to an alternate approach, namely to include on-chip circuitry that can decode a modulated light signal and can therefore be activated by a coded signal. The advantage of this is that many more devices can be addressed separately.

These microfabricated electrostimulators are powered by near-infrared light (Near-IR), allowing for wireless activation in neural tissue. The implantable part of the system contains photovoltaic devices, an energy storage device, and circuitry for signal demodulation and excitation control. They are microfabricated to allow small device dimensions (on the order of 10 μm to 100 μm) to minimized tissue damage on implantation. When illuminated with infrared radiation they are capable of generating an electrical current to induce an action potential in neurons that are in close proximity to the device.

If the active areas are illuminated with infrared radiation, a voltage potential is generated between the anode and cathode. Because the neurostimulators are small, they are easily implanted in neural tissue with minimal damage to the tissue. If they are in close proximity to a neuron, the voltage potential generated between the anode and cathode will initiate an action potential in the neuron due to the resultant injected electrical charge.

Figure 3:
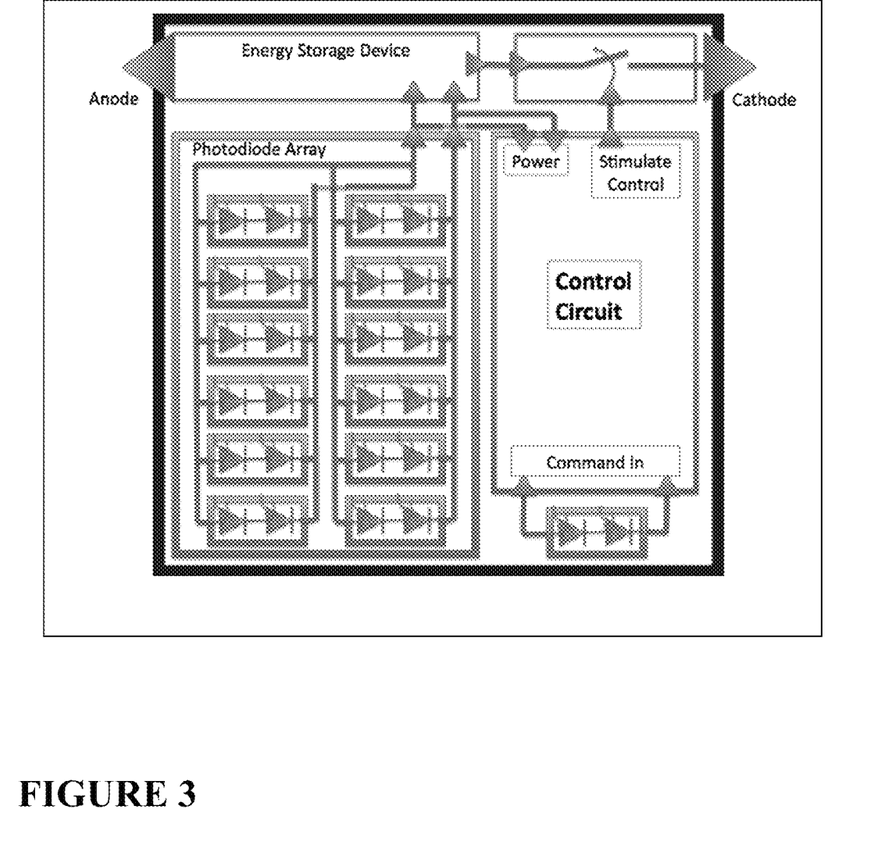
FIG. 3 depicts the top level schematic for the neurostimulators.

Near-IR is capable of penetrating neural tissue to a depth of several millimeters, making it possible to wirelessly stimulate the neurostimulators that are implanted into neural tissue. A possible setup is shown in FIG. 3 where the neurostimulators are implanted inside the neural tissue in close proximity to the dura mater and are irradiated by a near-IR source (in this case a VCSEL array) located outside the dura mater. Power and telemetry connections to the near-IR source are provided by a peripheral source.

Figure 2:
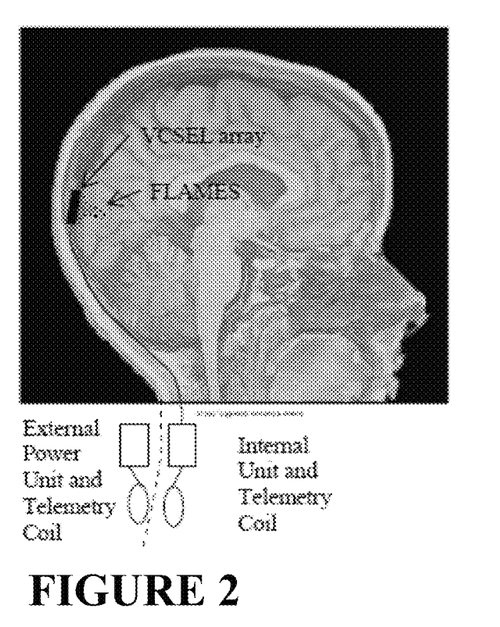
FIG. 2 shows a setup for wireless stimulation of FLAMES.

FIG. 2 depicts the top level schematic for the neurostimulators. The neurostimulators contain an array of photodiodes to charge an energy storage device, which generates an electric potential between anode and cathode. The energy storage device is charged by an array of photodiodes, which can be series connected to attain high voltage potentials. This energy storage device powers a control circuit, which has an input for a modulated control signal for addressability of individual neurostimulators. The modulated signal can be transmitted wirelessly via led emitters, e.g. LEDs, thus allowing addressability through a modulated output of the infrared radiation source. Upon activation, the control circuitry will connect the energy storage device to the anode and cathode to generate a voltage potential and resulting in charge injection to the neural tissue to initiate an action potential.

In one embodiment of the present invention a Smart FLAMES device can create potentials on the order of about one volt and run at rates exceeding 5 kHz if desired. The stimulation duty cycle can approach up to about 40% for said embodiment.

Figure 4:
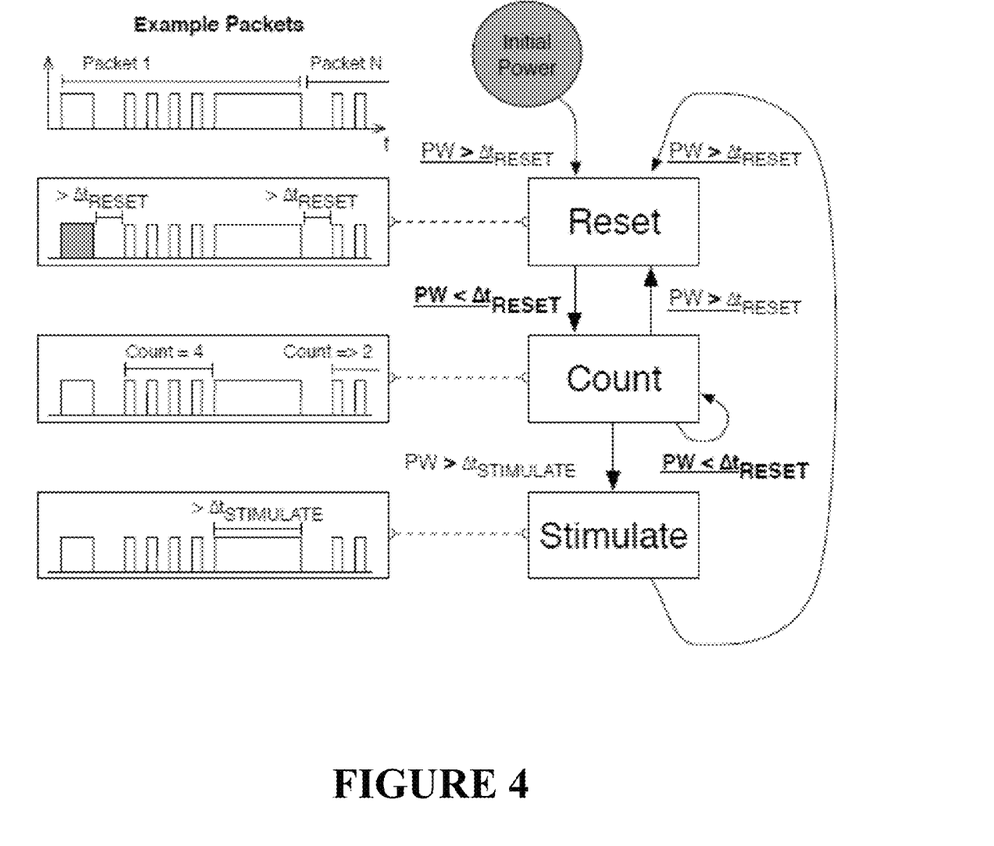
FIG. 4. depicts a state diagram for the different states as well as exemplary waveforms of the typical optical packet.

The logical operation of certain embodiments of the present invention follows FIG. 4. For these embodiments, absent any signal long enough to discharge the energy stored in the device's supply capacitance, the device enters the initial power state and requires a pulse to "wake-up". The duration of this pulse must be at least long enough to bring the supply voltage to the expected supply voltage of approximately 1.2V-to approximately 1.4V, which has been shown to be in the preferred range of about 4-to about-5 μs for said embodiments.

For said embodiments, once the pulse is off for longer than $\Delta t_{PACKET}$, the device enters a known steady-state, the reset state, and following this, is a series of short pulses that have an off-time less than $\Delta t_{RESET}$. For said embodiment, each short pulse iterates a count, starting from zero, on the count block circuitry with the maximum number of independent addresses determined by the number of count circuits that can be fit on a stimulator of said embodiment. After the targeted address has been pulsed the correct number of times, a long pulse will deliver the necessary charge to initiate a controlled stimulation for said embodiments. If the pulse is off for greater then $\Delta t_{RESET}$ the device goes back to reset state and waits for the next correct sequence, and if the device does not receive the correct count and long stimulate pulse, it does not attempt to do anything and will always enter the reset state after the control signal is off for $\Delta t_{RESET}$. In said embodiments, because the stimulus pulse occurs shortly after the pulsing portion of the packet, the time between activation of different addresses is variable and is dependent on the address ID number. Therefore, in these embodiments, a device which is unselected will not enter the stimulated state and return to the reset state after the control signal is off for $\Delta t_{RESET}$.

In another embodiment of the present invention, after initial powering up from either a short pulse or after a stimulate pulse, a microstimulator enters the reset state after the pulse is off for greater then $t_{RESET}$. Then, for said embodiment, said microstimulator will receive a specified number of short pulses during the count state. Subsequently, a long pulse ($t_{STIMULATE}$) delivers the electric energy needed for stimulation, as illustrated in the transition from count state to the stimulate state as seen in FIG. 4. For said embodiment, if the address ID matches the pulsed count then the output is enabled during this time. After the stimulate pulse, the device of one embodiment of the present invention returns to the reset state and then the process is repeated.

To decode and utilize the optical packets of certain embodiments of the present invention, the system can be divided into four functional blocks: optical power and controls, reset detection, pulse counting, and stimulation. In one embodiment of the present invention, the optical power and controls provide the external inputs and operating voltages needed to use the circuits while the reset detection and pulse counting stages control the functional state of the device, with the stimulation block controlling the output signal, a large voltage pulse that is used to stimulate neural tissue. Together these functional blocks contain all the necessary circuitry to power and control the microdevice using encoded optical pulses.

Figure 5:
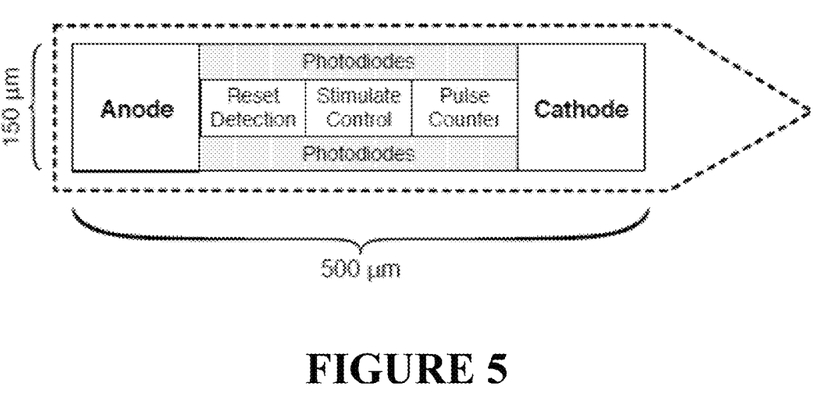
FIG. 5 illustrates the floor plan for embodiments of the present invention.

The floor plan of an exemplary Smart FLAMES is shown in FIG. 5. The basic shape with anode and cathode at opposite ends of the device has been studied and it was found that the voltage field in a volume conductor for any device size and current can be predicted as long as the aspect ratios are maintained; a typical aspect ratio is between three-to-five. The anode and cathode contacts are placed on opposite ends of the device for the exemplary embodiment depicted in FIG. 5 to maximize the stimulation effect in the neural tissue. As seen in FIG. 5, the critical circuitry is enclosed in the center and contains the reset detection, stimulation control, and pulse counting blocks with the logic circuitry surrounded by photodiodes to generate the necessary voltages for stimulation and circuit operation. In FIG. 5 the dotted outline indicates the device geometry. In said embodiment a pointed tip facilitates insertion into the tissue.

The photodiode power and control block has three sets of photodiodes for one embodiment of the present invention. In this embodiment, the first is a set of photodiodes to generate the current for stimulation of the neural tissue, the second set contains photodiodes to provide the necessary voltage to run the logic circuits, and the third photodiode set contains photodiodes with a resistive load to pulse shape the input so it can be used as a control signal. The output of this pulse shaping photodiode is the input for a two-stage inverter pair/buffer that supplies the control pulse to the other functional blocks with the buffered pulses used as inputs for the reset detection, counter, and stimulation stages.

In one embodiment of the present invention, the reset detection stage is used to reset the counter and puts the circuit and logic into a known idle state while activation of the reset detection stage is done with an absence of a pulse for at least $t_{RESET}$ after any length pulse. This requires rapid pulsing by the count stage to prevent the device from incorrectly returning to the reset state, but advantageously allows the device to automatically reset after the end of each stimulation phase.

In said embodiment, the counter stage has a finite number of count circuit elements, the number of which determines the maximum number of addressable stimulators, which will vary depending on the application. It may change from a few stimulators in the spinal cord to hundreds in the brain cortex. For example, one may implant from 1 to about 5 stimulators in the spinal cord. Alternatively, for applications that require stimulation in the brain cortex, the number of stimulators required will be determined by the condition to be treated. For example, a condition that requires localized stimulation may require from about 10 to about 150 stimulators. Other conditions may require from about 100 to about 800 stimulators. For use as a visual prosthesis, from about 600 to about a thousand stimulators may be required. Other applications may require up to a million stimulators. The counter circuit is based on CMOS dynamic logic, whereby an initial state is setup through the use of complementary reset signals that are provided by the reset detection stage. In said embodiment, the stimulate stage contains a series of photodiodes controlled by a NAND logic gate with the two inputs to the NAND gate activating the stage when the specific address is active in concert with a long positive pulse. In said embodiment, the long pulse detector is simply two long NMOS devices, whose gates are tied to the shaped input pulse, connected in series to a capacitor which delays the NAND gate from triggering on any short pulses, such as the count pulse. In said embodiment, the specific address input of the NAND gate is a connection to a specific count stage. For example, for the fourth address of a Smart FLAMES device of one embodiment of the present invention, the input would be connected to the output of the fourth count block and each said device can only respond to one specific count, i.e. address ID.

The penetration depth of said device is variable and because the amount of attenuation of near infrared (NIR) light, has a direct effect on the amount of absorbed power from an illumination source; the device must be able to work across a large range of supply conditions.

Figure 6:
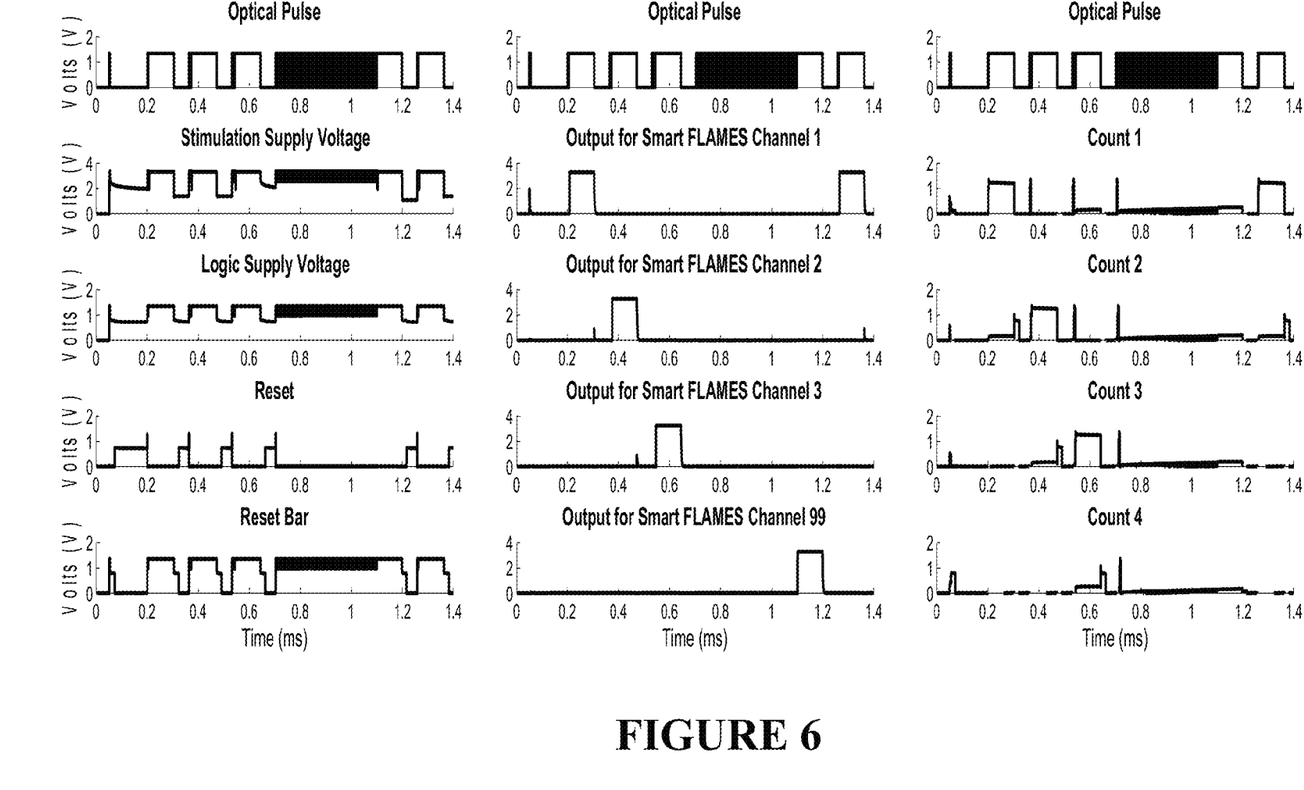
FIG. 6 depicts simulated response of Smart FLAMES to a wake-up pulse, followed by five packets. Packet one, two, and three target Smart FLAMES addresses one, two, and three respectively. The fourth packet activates the $99^{th}$ address. The last packet activates address one again.

As shown in FIG. 6, in one embodiment of the present invention, shortly after the initial power-on pulse, complementary reset signals are activated, causing the system to reset by setting all count circuits inactive (low) which occurs when the microstimulator device of said embodiment is operating off stored energy on the supply voltage's decoupling capacitor; during this time the supply voltage decays exponentially. In said embodiment, after reset, the count pulses go off in order for the appropriate count stage. In said embodiment, they activate after the high-to-low transition and then deactivate following the subsequent low-to-high transition. When the previous count value is active (high) during the positive portion of a pulse, the next count can transition and becomes the active count for said embodiment. The stimulus portion of the packet comes after the correct count of a targeted device. This can cause a stimulus current to be applied to the contacts of the device in said embodiment. And after the stimulus portion of the packet transitions from high-to-low, the logic resets the device to the reset state and waits for another packet or eventually dissipates any remaining energy for said embodiment of the present invention.

In one embodiment of the present invention an initial wake-up pulse must be supplied to activate the electronic circuits; the duration of the wake-up pulse is 20 µs. Subsequently, short pulses determine or count the specific channel number that should be selected; these pulse periods are typically 2-to-4 µs for said embodiment while a longer stimulation pulse delivers the necessary power to induce stimulation, and this process can be repeated rapidly within 50-to-100 µs if desired.

The feasibility of such a device must also be able to be used in range of parameters it will face in the CNS. In one embodiment of the present invention, the device operates at speeds consistent with neural activity, that is, a stimulation pulse every 50-to-100 ms, with a 5 µs-to-200 µs pulse width. In said embodiment, to maximize collection of optical energy, the photodiode surface area will occupy all available area after the control circuitry and electrode contacts have been placed.

Although the systems and methods of the present disclosure have been described with reference to exemplary embodiments thereof, the present disclosure is not limited thereby. Indeed, the exemplary embodiments are implementations of the disclosed systems and methods are provided for illustrative and non-limitative purposes. Changes, modifications, enhancements and/or refinements to the disclosed systems and methods may be made without departing from the spirit or scope of the present disclosure. Accordingly, such changes, modifications, enhancements and/or refinements are encompassed within the scope of the present invention.

We claim:

1. An addressable wireless implantable micro-electrical stimulator which comprises a photovoltaic device, an energy storage device and circuitry for signal demodulation and excitation control wherein the stimulator contains a control circuit that decodes a signal received by the stimulator and determines whether the stimulator is to be activated or not activated, wherein the stimulator is addressed by the signal a one-way communication channel that transmits the signal via an encoded optical pulse packet to the control circuit, wherein the control circuit is divided into functional blocks which control functions of the stimulator, which functions are comprised of optical power and controls, reset detection, pulse counting, and stimulation, and wherein the optical power and controls includes sets of photodiodes, a first one of sets of photodiodes is connected in series to generate the stimulation current, a second one of the sets of photodiodes is connected in series to generate voltage to run logic circuits, and a third one of the sets of photodiodes is in series with a resistive load to pulse shape an input.

2. The stimulator of claim 1 which is powered by conversion of near infrared radiation produced by an external source.

3. The stimulator of claim 1, wherein the signal corresponds to a modulated light signal and the circuitry further comprises an anode and a cathode, the circuitry selectively connects the energy storage device to the anode and the cathode to generate a voltage potential in response to receiving the modulated light signal, the modulate light signal including a sequence of pulses corresponding to an address identifier of the stimulator and an activation signal for the stimulator.

4. The stimulator of claim 1, wherein the signal corresponds to a single modulated light signal and an addressability and stimulation of the stimulator occur in response to receipt of the single modulated light signal.

5. The stimulator of claim 4, wherein the addressability of the stimulator corresponds to a first portion of the single modulated light signal and the stimulation corresponds to a second portion of the single modulated light signal.

* * * * *

UNITED STATES PATENT AND TRADEMARK OFFICE
CERTIFICATE OF CORRECTION

PATENT NO. : 9,526,904 B2  
APPLICATION NO. : 13/871654  
DATED : December 27, 2016  
INVENTOR(S) : Mesut Sahin et al.

It is certified that error appears in the above-identified patent and that said Letters Patent is hereby corrected as shown below:

Column 1, Lines 13-17 -- STATEMENT REGARDING FEDERALLY SPONSORED RESEARCH --
Remove: -- The research leading to the present invention was supported, in part by federal grants including the NIH Grants NIH R21-NS 050757-01A1 and NIH/NIBIB R01 EB009100-01. Accordingly, the United States Government may have certain rights in the invention. --
Insert: -- This invention was made with government support under NIH/NIBIB R01 EB009100-01 awarded by the National Institutes of Health. The government has certain rights in the invention. --

Signed and Sealed this  
Fifth Day of June, 2018

Andrei Iancu  
*Director of the United States Patent and Trademark Office*